United States Patent [19]

D'Silva

[11] 4,124,721

[45] Nov. 7, 1978

[54] PESTICIDAL UNSYMMETRICAL BIS-ARYLCARBAMATE SULFIDE COMPOUNDS CONTAINING A 2,3, DEHYROBENZOFURAN GROUP

[75] Inventor: Themistocles D. J. D'Silva, South Charleston, W. Va.

[73] Assignee: Union Carbide Corporation, New York, N.Y.

[21] Appl. No.: 803,280

[22] Filed: Jun. 3, 1977

[51] Int. Cl.$^2$ .................... C07D 307/86; A01N 9/12
[52] U.S. Cl. .................................. 424/285; 424/275; 424/282; 260/330.5; 260/340.5 R; 260/346.73
[58] Field of Search ............ 260/346.73, 340.5, 330.5; 424/275, 282, 285

[56] References Cited

U.S. PATENT DOCUMENTS

| | | | |
|---|---|---|---|
| 3,679,733 | 7/1972 | Brown et al. | 560/134 |
| 3,794,733 | 2/1974 | Brown et al. | 424/300 |
| 3,929,838 | 12/1975 | Siegle et al. | 260/346.73 |

OTHER PUBLICATIONS

Fahmy et al., J. Agr. Food Chem., vol. 22, No. 1, 1974, pp. 59–62.

*Primary Examiner*—Henry R. Jiles
*Assistant Examiner*—Bernard Dentz
*Attorney, Agent, or Firm*—Richard C. Stewart

[57] ABSTRACT

Unsymmetrical bis-[N-alkyl-N-arylcarbamate] sulfide compounds exhibit outstanding miticidal, nematocidal and insecticidal activity, coupled with substantially reduced mammalian toxicity and phytotoxicity.

18 Claims, No Drawings

PESTICIDAL UNSYMMETRICAL BIS-ARYLCARBAMATE SULFIDE COMPOUNDS CONTAINING A 2,3, DEHYROBENZOFURAN GROUP

SUMMARY OF THE INVENTION

This invention relates to a novel class of unsymmetrical bis-arylcarbamate sulfide compounds and to methods of preparing them. This invention also relates to insecticidal, nematocidal and miticidal compositions comprising an acceptable carrier and an insecticidally or miticidally effective amount of a compound of this invention as well as to a method of controlling insects, mites and nematodes by subjecting them to an insecticidally, miticidally or nematocidally effective amount of a compound of this invention.

The bis-carbamate compounds of this invention exhibit wide spectrum high level insecticidal activity as well as relatively low mammalian toxicity. This unique combination of high insecticidal activity and low mammalian toxicity permit the use of the novel unsymmetrical bis-carbamate compounds of this invention in relative safety.

DESCRIPTION OF THE INVENTION

This invention relates to compounds of the formula:

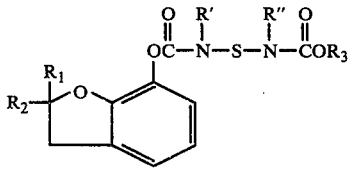

wherein:
$R'$ and $R''$ are the same or different and are alkyl having from 1 to 4 carbon atoms;
$R_1$ and $R_2$ are individually hydrogen or alkyl having from 1 to 4 carbon atoms;
$R_3$ is:
(A) naphthyl, benzodioxolanyl, tetrahydronaphthyl, indanyl or benzothienyl, all of which may be either unsubstituted or substituted with one or more alkyl groups.
(B.) phenyl either unsubstituted or substituted with one or more alkyl having from 1 to 12 carbon atoms, alkoxy, alkylthio, alkylsulfinyl, alkylsulfonyl, alkylthioalkyl, alkylsulfinylalkyl, alkylsulfonylalkyl, dialkylamino or nitro groups;
with the proviso that $R_3$ may not include more than eight aliphatic carbon atoms, except as noted.

Other compounds which are illustrative of the new compounds of this invention are:
N-[2,3-Dihydro-2,2-dimethyl-7-benzofuranyl methylcarbamate] N-[3-(1-methylpropyl)phenyl methylcarbamate] sulfide.
N-[2,3-Dihydro-2,2-dimethyl-7-benzofuranyl methylcarbamate] N-[(4-dimethylamino-3,5-xylylmethylcarbamate] sulfide.
N-[2,3-Dihydro-2-methyl-7-benzofuranylmethylcarbamate] N-[2-isopropoxyphenyl methylcarbamate] sulfide.
N-[2,3-Dihydro-2,2-dimethyl-7-benzofuranylmethylcarbamate] N-[4-benzothienyl methylcarbamate] sulfide.
N-[2,3-Dihydro-2,2-dimethyl-7-benzofuranylmethylcarbamate] N-[5,6,7,8-tetrahydronaphthyl methylcarbamate] sulfide.
N-[2,3-Dihydro-2,2-dimethyl-7-benzofuranylmethylcarbamate] N-[3,4,5-trimethylphenyl methylcarbamate] sulfide.
N-[2,3-Dihydro-2,2-dimethyl-7-benzofuranylmethylcarbamate] N-[4-methylthio-3,5-xylylmethylcarbamate] sulfide.
N-[2,3-Dihydro-2,2-dimethyl-7-benzofuranylmethylcarbamate] N-[4-dimethylamino-3-tolyl methylcarbamate] sulfide.
N-[2,3-Dihydro-2,2-dimethyl-7-benzofuranyl methylcarbamate] N-[4-indanylmethylcarbamate] sulfide.
N-[2,3-Dihydro-2,2-dimethyl-7-benzofuranyl methylcarbamate] N-[2-ethylthiomethylphenyl methylcarbamate] sulfide.
N-[2,3-Dihydro-2,2-dimethyl-7-benzofuranyl methylcarbamate] N-[2-ethylsulfinylmethylphenyl methylcarbamate] sulfide.
N-[2,3-Dihydro-2,2-dimethyl-7-benzofuranyl methylcarbamate] N-[4-methylsulfinyl-3,5-xylylmethylcarbamate] sulfide.
N-[2,3-Dihydro-2,2-dimethyl-7-benzofuranyl methylcarbamate] N-[3,5-diisopropylphenyl methylcarbamate] sulfide.
N-[2,3-Dihydro-2,2-dimethyl-7-benzofuranyl methylcarbamate] N-[2,2-dimethylbenzodioxolanyl-4-methylcarbamate] sulfide.

All of the compounds within the purview of the generic formula set forth above exhibit miticidal and insecticidal activity to a lesser or greater extent. Accordingly, these compounds are extremely useful for the control of insect, nematode and mite pests. Some of these compounds exhibit very high levels of miticidal, nematocidal and insecticidal activity in extremely small dosages while others require larger dosages to be effective.

In general, the compounds of this invention are either totally lacking in phytotoxicity or exhibit only minimal phytotoxicity with respect to economically important crop species. In addition, these compounds exhibit substantially reduced levels of mammalian toxicity as compared to known pesticidal compounds having a comparable spectrum of activity against insect, arachnid and nematode pests.

Preferred because of their higher levels of miticidal and insecticidal activity are the compounds of this invention in which:
$R'$, $R''$, $R_1$ and $R_2$ are methyl;
$R_3$ is naphthyl, or phenyl substituted with one or more alkoxy, alkyl, alkylthio or dialkylamino groups.

The unsymmetrical bis-[N-alkyl-N-arylcarbamate] sulfide compounds of this invention can be conveniently prepared by a variety of methods. One preferred method is illustrated by the reaction scheme set forth below in which $R'$, $R''$, $R_1$, $R_2$ and $R_3$ are as described above, except as noted:

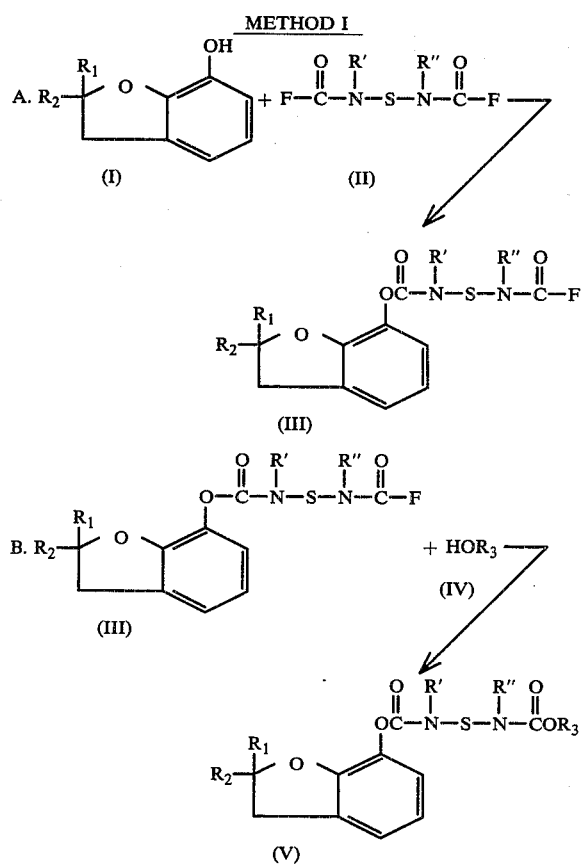

METHOD I is a two-step reaction sequence which can be conducted either in-situ or the carbamate-sulfenyl carbamoyl halide intermediate (III) of Step A can be isolated and used as the reactant of Step B at some latter time. In Step A, one equivalent of an appropriately substituted hydroxyl reactant, either 2,2-dimethyl-2,3-dihydrobenzofuran-7-ol or $R_3OH$ is reacted with one equivalent of the bis-(N-alkyl-N-fluorocarbonylamino) sulfide reactant (II), in the presence of at least one equivalent of an acid acceptor, preferably in an aprotic solvent to yield the intermediate carbamate sulfenyl carbamoyl halide (III). In Step B, an equivalent of the intermediate carbamate sulfenyl carbamoyl halide (III) reactant is then reacted with second equivalent of a hydroxyl reactant, $R_3OH$ if 2,2-dimethyl-2,3-dihydrobenzofuran-7-ol was used as the hydroxyl reactant in step A or 2,2-dimethyl-2,3-dihydrobenzofuran-7-ol if $R_3OH$ was used as the hydroxyl reactant of Step A. Step B is also conducted in the presence of at least one equivalent of an appropriate acid acceptor and in an aprotic solvent, to yield the desired bis-arylcarbamate compound (V).

The reactions of METHOD I is normally conducted in an aprotic organic solvent. Illustrative of aprotic organic solvents which are suitable as reaction solvents in the practice of the preferred embodiments of this invention are saturated and unsaturated aliphatic and aromatic hydrocarbons, e.g. hexane, cyclohexane, octane, dodecane, naphtha, decalin, kerosene, tetrahydronaphthalene, benzene, toluene, xylene, naphthalene, alkylnaphthalene, or the like, ethers such as tetrahydrofuran, tetrahydropyran, diethyl ether, dioxane, 1,2-dimethoxybenzene, 1,2-ethoxybenzene, the dialkyl ethers of ethylene glycol, of butylene glycol, or diethylene glycol, of dipropylene glycol, or chlorinated aliphatic hydrocarbons as for example, chloroform, dichloromethane, carbon tetrachloride or the like.

The acid acceptor utilized in the conduct of the reaction of METHOD I may be either an organic or inorganic base. Illustrative of organic bases that are useful as acid acceptors are tertiary amines, alkali metal alkoxides or the like. Bases such as sodium hydroxide, potassium hydroxide or the like are illustrative of inorganic bases which are useful in the conduct of this reaction. Preferred acid acceptors are aromatic and aliphatic tertiary amines, such as triethylamine, pyridine, trimethylamine, 1,4-diazobicyclo [2.2.2] octane and the like.

When an inorganic base is used as the acid acceptor, phase transfer agents may be used to facilitate the transfer of the acid acceptor across the organic/inorganic phase interface. Illustrative of useful phase transfer agents are crown ether compounds, quaternary ammonium halide compounds or the like.

In these reactions, the reaction temperature is not critical and can be varied over a wide range. The reaction is preferably conducted at a temperature of from about $-30°$ C. and upwards to approximately 130° C. Particularly preferred reaction temperatures are from about 0° C. to about 75° C.

Reaction pressures are not critical. The process can be conducted at either subatmospheric, atmospheric or superatmospheric pressure. For convenience the reaction is usually conducted at atmospheric or autogeneous pressure.

Hydroxylated aryl compounds employed as reactants in the reactions of METHOD I are well known compounds that can be prepared by well known synthetic procedures or obtained from commercial sources.

The bis-(N-alkyl-N-fluorocarbonylamino) sulfide precursors can be conveniently prepared by reacting sulfur dichloride with N-alkylcarbamoyl fluoride in toluene in the presence of an acid acceptor as for example triethylamine or pyridine. This procedure is described in more detail in U.S. Pat. No. 3,639,471.

The following specific examples are presented to particularly illustrate the invention:

EXAMPLE I

Preparation of Bis-(N-Methyl-N-fluorocarbonylamino) sulfide

To a polyethylene reactor containing 80 g (4.0 m) of hydrogen fluoride in 1800 ml of toluene, cooled to $-40°$ C. was added dropwise with stirring 228 g (4.0 m) of methyl isocyanate, over a period of 20 min. The reaction mixture was allowed to warm to 0° C. and was maintained at this temperature for 1 hr. Then 206 g (2.0 m) of freshly distilled sulfur dichloride was added followed by a slow addition of 346 g (4.4 m) of pyridine at $-20°$ to 1° C. After stirring for 2 hrs. at $-10°$ C. and for 16 hrs. at ambient temperature, the reaction mixture was diluted with 500 ml of water. The toluene layer was further washed with (3 × 500 ml) water, dried and distilled to afford 244 g (66 percent) of the product. B.p 55°–57° C./0.25 mm. On standing the distillate crystallized. m.p. 40°–41° C.

Calc'd for $C_4H_6F_2N_2O_2S$: C, 26.09; H, 3.28; N, 15.21
Found: C, 26.19; H, 3.20; N, 14.79

EXAMPLE II

Preparation of
2,2-Dimethyl-2,3-dihydro-7-[N-methyl-N(N-'-methyl-N'-fluorocarbonylaminosulfenyl) carbamoyloxy] benzofuran To a solution of 5.0 g of bis-(N-methyl-N-fluorocarbonylamino) sulfide, prepared as Example I, and 5.0 g of 2,2-dimethyl-2,3-dihydrobenzofuran-7-ol in 75 ml of dioxane, was added 4.0 g of triethylamine. After allowing the reaction mixture to stand at ambient temperature for 6 days, it was diluted with 200 ml of water and extracted in ethyl acetate. The ethyl acetate extract was washed with water, dried and concentrated under vacuo. Purification by silica gel chromatography afforded 5.0 g of 2,2-Dimethyl-2,3-dihydro-7-[N-methyl-N-(N'-methyl-N'-fluorocarbonyl-aminosulfenyl) carbamoyloxy]benzofuran as a viscous oil.

Calc'd for $C_{14}H_{17}FN_2O_4S$: C, 51.21; H, 5.21; N, 8.53
Found: C, 51.90; H, 5.34; N, 8.60

EXAMPLE III

Preparation of
[N-Methyl-N-(N'-methyl-N'-fluoroformylaminosulfenyl)carbamoyloxy]naphthalene To a solution of 4.32 g of 1-naphthol in 25 ml of dioxane was added 6.0 g of bis-(N-methyl-N-fluorocarbonylamino) sulfide, prepared as in Example I. To this solution added dropwise with stirring 3.03 g of triethylamine diluted with 5.0 ml of dioxane. After stirring for 28 hrs. at room temperature the solution was concentrated under reduced pressure and then taken in ethyl acetate, washed with water, dried over magnesium sulfate and concentrated to 7.22 g of an oil. [N-Methyl-N-(N'-methyl-N'-fluoroformylaminosulfenyl) carbamoyloxy]naphthalene crystallized from isopropyl ether, m.p. 58°-60° C.

Calc'd for $C_{14}H_{13}FN_2O_3S$: C, 54.53; H, 4.25; N, 9.09
Found: C, 54.58; H, 4.32; N, 8.96

EXAMPLE IV

Preparation of
[2,2-Dimethyl-2,3-dihydro-7-benzofuranyl methylcarbamate]N-[4-t-butylphenylmethylcarbamate]sulfide To a solution of 5.0 g (0.017m) of 2,2-dimethyl-2,3-dihydro-7-[N-methyl-N'-fluorocarbonylaminosulfenyl) carbamoyloxy]benzofuran (prepared as in Example II), and 2.55 g (0.017 m) of 4-tert-butylphenol in 100 ml of toluene, was added 1.7 g of triethylamine. The reaction mixture was heated for 8 hrs. at 50°-60° C. and then allowed to stand overnight at room temperature. The mixture was washed with dilute sodium hydroxide followed by water until the wash was neutral. It was dried over magnesium sulfate and concentrated. The product crystallized from isopropyl ether solution to afford 3.5 g of [2,2-Dimethyl-2,3-dihydro-7-benzofuranyl methylcarbamate] N-[4-t-butylphenyl methyl carbamate] sulfide as a white solid, m.p. 130°-131.5° C.

Calc'd for $C_{24}H_{30}N_2O_5S$: C, 62.86; H, 6.59; N, 6.11
Found: C, 62.76; H, 6.59; N, 6.11

Selected species of the new compounds were evaluated to determine their pesticidal activity against nematodes, mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thusprepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°-70° F. and 50-70 percent relative humidity, constituted the test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids, were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°-70° F. and 50-70 percent, respectively. Aphids which fell onto the paper and were unable to remain standing after being uprighted were considered dead. Aphis remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (*Prodenia eridania*, (Cram.)), reared on Tendergreen bean plants at a temperature of 80°±5° F. and a relative humidity of 50±5 percent, constituted the test insects.

The test compounds were formulated by diluting the stock suspension with water to given a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for three days. Although the larvae could easily consume the whole leaf within 24 hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle *Epilachna varivestis, Muls.*), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica,* L.) reared according to the specifications of the Chemical Specialties Manufacturing Association (Blue Book, McNair-Dorland Co., N.Y. 1954; pages 243-244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for 24 hours, at a temperature of 80°±5° F. and the relative humidity of 50±5 percent. Flies which showed no sign of movement on prodding were considered dead.

Mite Foliage Spray Test

Adults and nymphal stages of the two-spotted mite (*Tetranychus urticae* Koch), reared on Tendergreen bean plants at 80±5 percent relative humidity, were the test organisms. Infested leaves from a stock culutre were placed on the primary leaves of two bean plants six to eight inches in height, growing in a two- and-a-half inch clay pot. 150-200 Mites, a sufficient number for testing, transferred from the excised leaves to the fresh plants in a period of twenty four hours. Following the 24 hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for 6 days, after which a mortality count of motile forms was made. Microscopic examination for motile forms was made on the leaves of the test plants. Any individual which was capable of locomotion upon prodding was considered living.

The results of these tests are set forth in Table I below. In these tests the pesticidal activity of the compounds against aphid, mite, Southern Armyworm, Bean Beetle and House Fly was rated as follows:

A = excellent control
B = partial control
C = no control
Dashes indicate no test conducted.

Certain of these compositions were also evaluated to determine their peroral toxicity to mammals. The animal selected for this experiment was the rat. The test results obtained are expressed in terms of the number of milligrams of compositions per kilogram of weight of the animal required to achieve a mortality rate of 50 percent ($LD_{50}$).

The results of these experiments are summarized and set forth in Table I, below.

TABLE I

| | PHYSICAL AND BIOLOGICAL PROPERTIES | | | | | | |
|---|---|---|---|---|---|---|---|
| | | | | BIOLOGICAL ACTIVITY | | | |
| COMPOUND | M.P° C | Bean Aphid | Mite | Southern Armyworm | Mexican Bean Beetle | House-fly | Rat mg/Kg |
| [2,2-Dimethyl-2,3-dihydro-7-benzo-furanyl methylcarbamate] N-[4-(tert-butyl) phenyl methyl carbamate]sulfide | 130-131.5 | A | C | A | A | A | 45 |
| [2,2-Dimethyl-2,3-dihydro-7-benzofuranyl methylcarbamate] N-[3-isopropylphenyl methyl-carbamate]sulfide | 121-123 | A | C | A | A | A | 80 |
| [2,2-Dimethyl-2,3-dihydro-7-benzofuranyl methylcarbamate] N-[naphthalenemethylcarbamate] | — | A | C | A | A | A | — |

TABLE I-continued
PHYSICAL AND BIOLOGICAL PROPERTIES

| COMPOUND | M.P° C | BIOLOGICAL ACTIVITY | | | | | Rat mg/Kg |
|---|---|---|---|---|---|---|---|
| | | Bean Aphid | Mite | Southern Armyworm | Mexican Bean Beetle | House-fly | |
| [2,2-Dimethyl-2,3-dihydro-7-benzofuranylmethylcarbamate] N-[3-methyl-4-methylthiophenyl methylcarbamate]sulfide | 126–127 | A | C | A | A | A | 18 |
| [2,2-Dimethyl-2,3-dihydro-7-benzofuranyl methylcarbamate] N-(4-nitro phenyl methylcarbamate] sulfide | 107–109 | A | C | A | A | A | 25 |
| [2,2-Dimethyl-2,3-dihydro-7-benzofuranyl methylcarbamate] N-[2-isopropoxyphenyl methylcarbamate]sulfide | 97–98 | A | C | A | A | A | — |
| [2,2-Dimethyl-2,3-dihydro-7-benzofuranyl methylcarbamate] N-[3-(dimethylamino)phenyl methyl-carbamate]sulfide | — | A | C | A | A | A | — |

The results set forth in TABLE I clearly show the broad spectrum pesticidal activity of the compounds of this invention, as well as their reduced mammalian toxicity. It will be understood that the insect and mite species employed in the above tests are merely representative of a wide variety of pests that can be controlled through the use of the compounds of this invention. A series of comparative tests were conducted to evaluate the relative biological properties of the compounds of the invention and certain prior art compounds. The test procedures employed are identical to those discussed above. The results of these experiments are summarized as set forth in Table II below. The results are reported in the parts per million of the compound required for a 50% kill (LD$_{50}$).

Compound 1 of TABLE II is the parent 2,3-dihydro-2,2-dimethyl-7-benzofuranyl methyl carbamate of the compounds of this invention. Compound 1 is known by the generic name carbofuran and is a well known, widely used commercial pesticide. Compound 2 is the symmetrical bissulfide derivative of the parent compound which had previously been described in the literature. Compounds 3, 4 and 5 are representative examples of the unsymmetrical bis-sulfide compounds of this invention.

TABLE II
COMPARATIVE LD$_{50}$ VALUES FOR INSECTS AND RATS

| No. | STRUCTURE | BIOLOGICAL PROPERTIES | | | | | |
|---|---|---|---|---|---|---|---|
| | | Aphid | Mite | Southern Armyworm | Mexican Bean Beetle | House-fly | Rat (mg/Kg) |
| 1 | [structure] | 2 | i | 90 | 12 | 12 | 5 |
| 2 | [structure] | 1 | i | 13 | 2 | 30 | 6.3 |
| 3 | [structure] | 1 | i | 20 | 3 | 22 | 80 |
| 4 | [structure] | 2 | i | 23 | 18 | 17 | 45 |

TABLE II-continued
COMPARATIVE LD$_{50}$ VALUES FOR INSECTS AND RATS

| | | BIOLOGICAL PROPERTIES | | | | | |
|---|---|---|---|---|---|---|---|
| No. | STRUCTURE | Aphid | Mite | Southern Armyworm | Mexican Bean Beetle | House-fly | Rat (mg/Kg) |
| 5 | 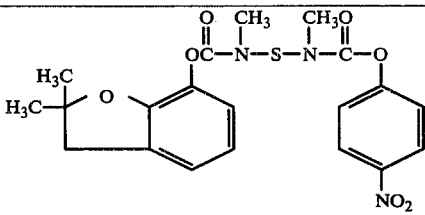 | 2 | i | 20 | 4 | 45 | 25.2 |

Examination of the data presented in Table II confirm the maintenance of insect toxicity of the previously known symmetrical bis-sulfide derivative at levels generally comparable to those of the parent compounds and even in some cases demonstrating slight improvements. However, the high level of mammalian toxicity of the prior art compounds is not acceptable. Note that the rat LD$_{50}$ (mg/kg) compound 1 is 5 and that the rat LD$_{50}$ (mg/kg) of the compound 2 is 6.3. These results are to be contrasted with the mammalian toxicity values exhibited by the novel compounds of this invention. Compound 3 had LD$_{50}$ value of 80 as compared to 5 for compound 1 and 6.3 for compound 2 and as such is at least 16 times less toxic to mammals than compound 1 and at least 13 times less toxic to mammals than compound 2. The increased mammalian safening effect is also exhibited by compounds 4 and 5. Compound 4 is nine times less toxic to mammals as compound 2 and seven times less toxic to mammals as compound 2. Compound 5 is five times less toxic to mammals as compound 1 and four times less toxic to mammals as compound 2. The increased mammalian safety is achieved while maintaining the high levels of insecticide and meticidal activity. At the same time it should be noted that the compounds of this invention exhibit low levels of toxicity against important economic crops. The compounds of this invention are unique among this entire class of compounds in their dramatically superior biological properties each as insect and mite toxicity, phytotoxicity and mammalian toxicity, the characteristics of which are critically determinative of the ultimate utility of an agricultural pesticide.

The compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid carriers with or without surface active agents. Liquid concentrates may be prepared by dissolving one of these compounds with a nonphytotoxic solvent such as acetone, xylene or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric, or cationic dispersing and emulsifying agents may be employed for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an approrpriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pound of active toxicant per acre.

The pesticides contemplated herein prevent attack by insects, nematodes and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicangs. The toxicants are so chemically inert that they are compatable with substantially any other constituents of the spray schedule, and they may be used in the soil, upon the seeds, or the roots of plants without injuring either the seeds of plants. They may also be used in combination with other pesticidally active compounds.

What is claimed is:

1. A compound of the formula:

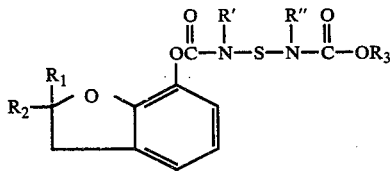

wherein:
R' and R" are the same or different and are alkyl having from 1 to 4 carbon atoms;
$R_1$ and $R_2$ are individually hydrogen or alkyl having from 1 to 4 carbon atoms;
$R_3$ is:
(A) naphthyl, benzodioxolanyl, tetrahydronaphthyl, indanyl or benzothienyl, all of which may be either unsubstituted or substituted with one or more alkyl groups.
(B) phenyl either unsubstituted or substituted with one or more alkyl having from 1 to 12 carbon atoms, alkoxy, alkylthio, alkylsulfinyl, alkylsulfonyl, alkylthioalkyl, alkylsulfinylalkyl, alkylsulfonylalkyl, dialkylamino or nitro groups;
with the proviso that $R_3$ may not include more than eight aliphatic carbon atoms, except as noted.

2. A compound according to claim 1 wherein R' and R" are methyl.

3. A compound according to claim 1 wherein $R_3$ is naphthyl or substituted phenyl wherein the permissible substituents are one or more alkyl, alkoxy, alkylthio, nitro or dialkylamino.

4. N-[2,3-Dihydro-2,2-dimethyl-7-benzofuranyl methylcarbamate] N-[1-naphthyl methylcarbamate] sulfide.

5. N-[2,3-Dihydro-2,2-dimethyl-7-benzofuranyl methylcarbamate] N-[3-isopropylphenyl methylcarbamate] sulfide.

6. N-[2,3-Dihydro-2,2-dimethyl-7-benzofuranyl methylcarbamate] N-[4-tert-butylphenyl methylcarbamate] sulfide.

7. An insecticidal and nematocidal composition comprising an acceptable carrier and as the active toxicant an insecticidally or nematocidally effective amount of a compound according to claim 1.

8. An insecticidal and nematocidal composition comprising an acceptable carrier and as the active toxicant an insecticidally or nematocidally effective amount of a compound according to claim 2.

9. An insecticidal and nematocidal composition comprising an acceptable carrier and as the active toxicant an insecticidally or nematocidally effective amount of a compound according to claim 3.

10. An insecticidal and nematocidal composition comprising an acceptable carrier and as the active toxicant an insecticidally or nematocidally effective amount of a compound according to claim 4.

11. An insecticidal and nematocidal composition comprising an acceptable carrier and as the active toxicant an insecticidally or nematocidacidally effective amount of a compound according to claim 5.

12. An insecticidal and nematocidal composition comprising an acceptable carrier and as the active toxicant an insecticidally or nematocidally effective amount of a compound according to claim 6.

13. A method of controlling insects and nematodes which comprises subjecting them to an insecticidally or nematocidally effective amount of compound according to claim 1.

14. A method of controlling insects and nematodes which comprises subjecting them to an insecticidally or nematocidally effective amount of compound according to claim 2.

15. A method of controlling insects and nematodes which comprises subjecting them to an insecticidally or nematocidally effective amount of compound according to claim 3.

16. A method of controlling insects, and nematodes which comprises subjecting them to insecticidally or nematocidally effective amount of compound according to claim 4.

17. A method of controlling insects, and nematodes which comprises subjectin them to insecticidally, or nematocidally effective amount of compound according to claim 5.

18. A method of controlling insects, and nematodes which comprises subjecting them to insecticidally, or nematocidally effective amount of compound according to claim 6.